(12) United States Patent
Hayoz

(10) Patent No.: US 10,758,354 B2
(45) Date of Patent: Sep. 1, 2020

(54) ADJUSTABLE ANNULOPLASTY DEVICE

(71) Applicant: KEPHALIOS S.A.S., Paris (FR)

(72) Inventor: Daniel Hayoz, Villars-sur-Glâne (CH)

(73) Assignee: KEPHALIOS S.A.S., Paris (FR)

(*) Notice: Subject to any disclaimer, the term of this patent is extended or adjusted under 35 U.S.C. 154(b) by 0 days.

(21) Appl. No.: 15/117,738

(22) PCT Filed: Jan. 29, 2015

(86) PCT No.: PCT/EP2015/051782
§ 371 (c)(1),
(2) Date: Aug. 10, 2016

(87) PCT Pub. No.: WO2015/121075
PCT Pub. Date: Aug. 20, 2015

(65) Prior Publication Data
US 2017/0007401 A1  Jan. 12, 2017

(30) Foreign Application Priority Data

Feb. 11, 2014 (EP) .................................. 14154581

(51) Int. Cl.
*A61F 2/90* (2013.01)
*A61F 2/24* (2006.01)

(52) U.S. Cl.
CPC ............. *A61F 2/2445* (2013.01); *A61F 2/90* (2013.01); *A61F 2250/001* (2013.01);
(Continued)

(58) Field of Classification Search
CPC ............ A61F 2/2445; A61F 2250/0003; A61F 2250/00014; A61F 2250/0018; A61F 2250/0029
See application file for complete search history.

(56) References Cited

U.S. PATENT DOCUMENTS 6,406,493 B1 * 6/2002 Tu .............................. A61F 2/06
623/2.37
8,556,965 B2   10/2013 Wright
(Continued)

FOREIGN PATENT DOCUMENTS

EP       2468215 A1   6/2012
JP    2011516209 A   5/2011
(Continued)

OTHER PUBLICATIONS

International Search Corresponding to PCT/EP2015/051782 dated Feb. 26, 2015.
(Continued)

*Primary Examiner* — Christopher D. Prone
(74) *Attorney, Agent, or Firm* — Davis & Bujold PLLC; Michael J. Bujold

(57) ABSTRACT

An adjustable annuloplasty device comprising a tube having a basically annular shape or adopted to be brought into an annular shape. At least one portion, preferably three portions, of an outer wall or the whole outer wall of the tube is more rigid than opposite portion(s) of an inner wall or the whole inner wall. The inner wall is arranged nearer to an inside area defined by the annular shape than the outer wall. The inner wall is adapted to be displaced inwardly at least along less rigid portion(s) of the circumference upon actuation by at least one actuation element while the outer wall remains basically constant.

11 Claims, 3 Drawing Sheets

Fig. 3

(52) U.S. Cl.
CPC .............. *A61F 2250/0003* (2013.01); *A61F 2250/0014* (2013.01); *A61F 2250/0018* (2013.01); *A61F 2250/0029* (2013.01); *A61F 2250/0036* (2013.01)

(56) References Cited

U.S. PATENT DOCUMENTS

| | | |
|---|---|---|
| 9,060,861 B2 | 6/2015 | Tozzi et al. |
| 9,295,553 B2 | 3/2016 | Padala et al. |
| 2010/0211166 A1 | 8/2010 | Miller et al. |

FOREIGN PATENT DOCUMENTS

| | | | |
|---|---|---|---|
| WO | 2009126629 A1 | 10/2009 | |
| WO | WO2009126629 A1 * | 10/2009 | .............. A61F 2/24 |
| WO | 2010/078121 A2 | 7/2010 | |
| WO | 2010078121 A2 | 7/2010 | |
| WO | 2012/019052 A2 | 2/2012 | |
| WO | 2012/084714 A2 | 6/2012 | |

OTHER PUBLICATIONS

Written Opinion Corresponding to PCT/EP2015/051782 dated Feb. 26, 2015.
Japanese Office Action issued in corresponding Japanese Patent Application No. 2016-551270 dated Jun. 18, 2018.

\* cited by examiner

ADJUSTABLE ANNULOPLASTY DEVICE

FIELD OF THE INVENTION

The present invention relates to an annuloplasty device. In some non-limiting examples, the invention relates to an adjustable annuloplasty device, for example, that can be adjusted within the body of a patient. Some non-limiting examples focus on treating atrioventricular cardiac valves such as the mitral valve or the tricuspid valve, but the concept, function and benefit are not limited to these valves.

BACKGROUND OF THE INVENTION

Annuloplasty (e.g. mitral or tricuspid annuloplasty) is the implantation of an annuloplasty device (e.g., mitral ring or tricuspid ring) to deform and/or reinforce the valve annulus to correct incompetent valve function. During a classical annuloplasty procedure, the surgeon sizes the valve annulus and chooses a fixed size annuloplasty device accordingly. This procedure is performed on the arrested heart under cardiopulmonary bypass. However, the effectiveness of a fixed-size annuloplasty device cannot be assessed during the procedure, because the heart is arrested. Only upon restarting the heart is it possible to assess whether the device has had the desired effect to correct valve function. If the repair has not been successful, the patient has to undergo a second operation. Without the second operation, there remain certain possible long term consequences of a certain level of residual regurgitation. A further limitation of the classical procedure is that, after implantation of an annuloplasty device, the size and geometry of the heart and the treated valve annulus may vary over time. Also for example, a dilated heart may respond to corrected valve function by returning to normal size. A fixed-size annuloplasty device may, over time, become ineffective or inappropriate for the size of the valve annulus causing recurrent mitral regurgitation and poor clinical outcome. The common practice is to implant too small rings in order to overcome the risk of residual regurgitation. Too small rings result also in other problems such as too little blood flow through the mitral valve called mitral stenosis.

Adjustable annuloplasty rings that may be adjusted after implantation in the body have been proposed. By way of example, WO 2012/084714 proposes a partly adjustable annuloplasty ring system able to achieve limited control of an effective shape of the ring. The annuloplasty ring is an assembly comprising an external support ring, an inner adjustable ring, a permanent pressing element mounted between the external and inner rings, and actuating means designed to slide the pressing element around a circumference between the inner and outer rings. The assembly is adjustable by controlling the actuator means to move the pressing element to a desired position around the circumference, in such a way that a specific part of the inner ring at that position is deformed inwardly. An advantage of the assembly using external and inner rings is said to be that the adjustment can be performed without reducing a perimeter length of the inner ring, thereby reducing risk of valve stenosis.

In addition to above issues, a yet further complication that may occur following mitral valve repair and implantation of a mitral ring, is the problem of systolic anterior motion (SAM) in which the anterior mitral valve leaflet deflects towards the septum. SAM can be a cause of potentially life-threatening left ventricular outflow tract obstruction (LVOTO). There are several theories about possible causes of SAM, including possible influence of mitral valve rings on the mitral valve anatomy. When medical treatment is unable to correct it, re-intervention is necessary to correct SAM.

SUMMARY OF THE INVENTION

The invention seeks to mitigate one or more of the above issues, in particular to provide an annuloplasty device with enhanced simplicity, versatility and custom adjustability.

According to the invention the problem is solved with the characterising features of the independent claims.

It is suggested to provide an adjustable annuloplasty device comprising a tube having a basically annular shape or adopted to be brought into an annular shape. At least one, preferably three, portions of an outer wall or the whole outer wall of the tube is more rigid than opposite portion(s) of an inner wall or the whole inner wall. The inner wall is the wall which is arranged nearer to a centre area of the tube than the outer wall. The inner wall is adapted to be displaced inwardly at least along less rigid portion(s) of the circumference upon actuation by one or more actuation elements while the outer wall remains basically constant, i.e. unchanged.

As used herein the term "tube" is intended to cover closed or partly open constructions, which means that the tube may have a cross section in a closed form generally in the form of an "O" or a "D", or a partly open form generally in the form of a "C" or an elongated "C".

A basically "annular shape" as used herein is intended to cover any shape for circumscribing at least a majority of a periphery of a valve annulus. An annular shape may be closed (e.g. generally "O" shaped or generally "D" shaped) or an annular shape may be open (e.g. generally "C" shaped). An annular shape does cover non round geometries (e.g. "D" shapes, elongated "C" shapes") as well as round geometries (e.g. generally "O" shaped or generally "C" shaped). An annular shape may be in a non planar 3D shape, e.g. generally a saddle shape. The annular shape may be three dimensionally bent "O", "C" or "D" shaped.

"Wall portions" and "wall parts" are used interchangeably herein.

The tube might be initially formed in basically annular shape or it might be adopted to be brought into the basically annular shape. Therefore, the tube might be initially in a generally linear shape but bendable and fixable into an annular shape. Other initial shapes than a straight linear shape are possible.

The tube might be brought into the annular shape before or after delivery. The tube might for example be delivered in a generally linear shape and bent around the annulus upon release from a delivery system.

The tube might be formed out of a planar sheet which is then rolled in order to achieve the tube.

The tube might be uniformly arranged along the whole circumference or it might be divided into separate parts. The separate parts might be connected with e.g. wires or struts or bars. The connecting parts might be part of the outer wall, wherein the inner wall is only present at the separated parts.

When in the annular shape, the tube comprises the inner wall and the outer wall. The inner wall is less rigid than the outer wall at least in one, preferably in three, portion of the tube. As a consequence of the difference in rigidity, the inner wall is displaceable at least at the less rigid portion(s) inwardly upon actuation by an actuation element while the outer wall remains basically constant.

The inner wall might be displaceable in every portion where the inner wall is less rigid than the opposite outer wall. Other portions of the inner and outer wall might have the same rigidity. In portions with the same rigidity no asymmetric expansion of the tube might be possible.

In embodiments wherein the whole inner wall is less rigid than the outer wall, the inner wall might be displaceable basically along its whole circumference. The inner wall might alternatively be displaceable only at along one or multiple, in particular three, less rigid portions of the circumference.

The tube is preferably constructed such as to withstand external unidirectional forces. The forces might be variable in intensity.

The adjustment of the inner wall is preferably a continuous deformation. Therewith, the inner wall can be deformed as much as needed. The inner wall does preferably not only have two discrete predefined positions or shapes to as e.g., in shape memory alloys but preferably has rather a plastic behaviour allowing for the continuous deformation.

The adjustment of the inner wall might be irreversible by e.g. irreversible deformation of the inner wall. The inner wall and preferably the whole tube, might preferably comprise and preferably is made of steel or "superplastic metal alloys" such as e.g. "superplastic titanium alloys". The inner wall and preferably the whole tube might alternatively comprise and preferably be made of a biocompatible plastic.

Alternatively, the adjustment, i.e. the deformation is reversible. The inner ring and preferably the tube might in this case be made of an elastic material. The actuation element might secure the inner wall in a displaced state.

Preferably the tube comprises an attachment component allowing the tube to be attached to the valve annulus. Preferably the attachment component is suturable, e.g. a fabric surrounding sleeve or a fabric layer allowing the ring to be sutured to the valve annulus.

Alternatively the ring might for example be glued or attached with clamps to the valve annulus.

The adjustment through displacement of the inner wall can take place either peri-operative or post-operative. The aim is to fine-tune the surgical results and eliminate either residual regurgitation or over-correction. In the post-operative mode, the valve area can be reduced in order to correct regurgitation and/or operating a more gradual size adjustment over time. Therewith, a long term treatment of the valve can be provided.

With such a construction the correction of the valve area is possible with a single tube and one or multiple actuation elements. There is no need for any further parts such as a second ring or the like. Therefore, the construction is simple and needs little material which results in lower costs and lower weight.

The actuation element might be moveable circumferentially between around at least parts of the circumference of the tube. Therewith, multiple parts of the inner wall might be displaced by one single actuation element. The tube may be constructed such that the inner wall may remain displaced when moving the actuation element to another place. After the inner wall has been displaced as wanted and the valve annulus has been correctly adjusted, the actuation element may be removed from the tube.

Alternatively, the different parts may be displaced by different actuation elements. The inner wall in this case would not necessarily need to remain displaced when the actuation element does not provide any force against the inner wall. Therewith, the inner wall may be re-adjusted if it has been displaced to a too large extent.

The actuation elements are preferably actuated by an actuator. The actuator remains outside the body of a patient during the operation. Preferably, the actuator is connected to the actuation element(s) with at least one transmission line. Depending on the actuation element different inputs, e.g. mechanical tension, liquids, electricity, heat etc. might be provided with the transmission line to activate the actuation element.

Preferably, the inner wall comprises at least one, preferably three, interruption whereby an outer wall portion(s) opposite the interruption(s) is continuous. The inner wall is able to be pivoted inwardly next to the interruptions upon the activation.

The interruptions of the inner wall provide less rigid inner wall portions compared to the opposite continuous portions of the outer wall. The inner wall next to the interruptions might be displaced, e.g. bent inwardly upon activation by an activation element.

The tube preferably comprises larger cells in the region of the interruptions than in the other regions. Larger cells provide less rigid portions than smaller cells. Therewith, regions of the inner wall next to the interruptions are bendable inwardly with less force.

Alternatively or additionally, the inner wall is thinner or made with a more flexible structure than the outer wall. The difference in thickness of the walls at least partly leads to the difference of rigidity of the walls. The difference in thickness may be the only cause for the difference in rigidity of the walls or it may work together with other causes.

Material of the inner wall might be removed after the tube is provided or the tube might be formed with a thinner inner wall from the beginning.

Alternatively and most preferred, the inner and outer walls have the same thickness and the difference in rigidity is achieved with another effect, as e.g. difference in materials or in structure.

The tube is preferably formed as a mesh structure with cells defined by stems. The inner wall preferably has larger mesh cells and/or thinner stems than the outer wall.

A mesh with bigger cells and/or thinner stems is bendable with less force than a mesh with smaller cells and/or thicker stems. The difference in the dimension of the mesh cells of the walls at least partly participates in the difference of rigidity of the walls. The different dimensions might be the only cause for the difference of they might act together with additional causes as e.g. the difference in thickness.

The asymmetric tube wherein the inner wall comprises larger mesh cells and/or thinner stems than the outer wall might be manufactured by cutting, preferably by laser cutting, the asymmetric mesh out of a solid tube.

Alternatively or additionally, the outer wall may comprise a support ring. The support ring might be arranged on the outside or inside of the basically annular tube. The support ring might be made of a different, more rigid material than the rest of the tube. Additionally or alternatively, the support ring might provide thickness to the outer wall to reinforce it. Therewith, the support ring at least partly participates in the difference in rigidity of the inner and outer walls. The support ring might be the only cause for the difference in rigidity of the support ring might act together with additional causes as e.g. the difference in thickness or difference in cell dimensions as described above.

The tube preferably comprises a memory shape material, in particular Nitinol. In a preferred embodiment, the tube is made of the memory shape material, in particular Nitinol.

Nitinol is a memory shape metal alloy known to have a good biocompatibility. Other biocompatible memory shape metals or metal alloys are usable with embodiments described herein. Additionally or alternatively, biocompatible plastics may be used.

Preferably the at least one actuation element is integratable or integrated into the outer wall.

A part of the at least one actuation element might serve as a section of the outer wall of the tube. The at least one actuation element therefore may be embedded in the outer wall and integrally formed with the tube.

Alternatively, the at least one actuation element is integrated into or onto the outer wall e.g. shortly before implantation. The outer wall might comprise at least one attachment site at which the at least one actuation element might be integrated.

The part of the at least one actuation element integrated into the outer wall may be more rigid than other parts of the actuation element. Hence, upon activation the at least one activation element will e.g. expand or deform inwardly to deform at least a part of the circumference of the inner wall of the tube while the outer wall is not deformed.

Alternatively, the at least one actuation element is integratable or integrated into the inner wall. A part of the at least one actuation element might serve as a section of the inner wall of the tube and an opposite part is arranged next to the outer wall. The at least one actuation element therefore may be embedded in the inner wall and integrally formed with the tube.

Alternatively, the at least one actuation element may be only integrated into the inner wall e.g. shortly before implantation. The inner wall might comprise at least one attachment site at which the at least one actuation element might be integrated or attached. Most preferably the actuator element is arranged within the tube in a space delimited by the outer and inner wall.

Actuation elements integrated into the inner may have a uniform rigidity. The rigidity of the actuation element is less than the rigidity of the outer wall. Upon activation, the actuation element will e.g. expand or deform inwardly because of the difference in rigidity of the actuation element and the outer wall.

Preferably there are three actuation elements which may be integrated into the inner or outer wall. Three elements been be shown to allow a variable and sufficient and stable deformation of the inner wall and hence the valve annulus.

Preferably the three actuation elements are arranged such that two actuation elements are at opposite lateral portions of the basically annular tube and one actuation element is arranged at the posterior portion of the basically annular tube.

The terms lateral and posterior portions relate to the place of the portions of the basically annular tube after implantation. Lateral portions of the basically annular tube will be arranged at or near lateral portions of the valve annulus after implantation, the posterior portion of the tube at or near the posterior portion of the annulus. Therefore, also a basically linear tube adopted to be brought into a basically annular tube has two lateral portions and one posterior portion.

These positions have been shown to be an optimal arrangement for a good deformation of the inner wall and the valve annulus with little deformation. Upon actuation, the lateral actuation elements are preferably moved first and the posterior actuation element only after the lateral portions have been adjusted.

The device is preferably actuatable with an activation element in the form of an inflatable bladder, preferably a balloon. In a preferred embodiment, the device comprises the inflatable bladder.

The inflatable bladder is arrangeable or arranged in the tube between the inner and outer wall. By inflating the bladder with a fluid, the bladder will expand. Because of the difference in rigidity of the inner an outer wall, inner wall will be displaced by the expanding bladder, wherein the outer wall remains basically unchanged. The inflatable bladder is preferably a balloon. Such inflatable balloons are e.g. known in the art from expandable stents.

The inflatable bladder is preferably moveable around the circumference of the tube in order to displace multiple parts of the inner wall with one single inflatable bladder. The inflatable bladder therefore is inflated to displace a part of the inner wall and then deflated to be moved to another place in the tube. The inner wall remains displaced after deflation of the bladder. After reaching the next place, the bladder is inflated again to displace a further part and afterwards deflated again. These steps are repeated until the valve annulus has been correctly adjusted. After adjusting the inner wall and therefore the valve annulus, the inflatable bladder may be removed from the tube. Preferably at least and in particular only the two lateral portions and the posterior portion of the valve annulus are adjusted.

With a movable actuation element, the inner ring might be displaced in any desired point. There is no need of predefined deforming regions. Therewith, the deformation of the inner ring can be better adjusted to the desired shape.

Alternatively, the inflatable bladder is not moveable and only displaces one area of the inner wall. In this case, preferably three blades are provided at predefined sites.

The inflatable bladder is preferably asymmetrical such that inflation of the bladder results in an asymmetric expansion. Therewith, the inner wall may be adjusted. To ensure the correct orientation of the inflatable bladder, the tube might itself comprise an asymmetric cross section matching the asymmetric inflatable bladder. The inflatable bladder is therewith oriented in the correct position at least upon a start of the inflation.

The inflatable bladder might comprise multiple inflatable lumens. Such an inflatable bladder is preferably arranged or arrangeable at least partly circumferentially around the tube such that the inflatable lumens are arranged at least partly circumferentially around the tube. Preferably, the single lumens are individually inflatable. Such an individual inflation might be achieved when the inflatable lumens are not fluidly linked and by providing a separate inflation port for each inflatable lumen.

The fluid may, for example, be a gas (e.g., for pneumatic control), or a liquid or gel (e.g., for hydraulic control). Preferably the fluid is a saline solution.

In one form, a hardenable fluid e.g. cement may be introducible. The extent of deployment of the fluid-deployable device may remain adjustable as long as the inflation fluid remains fluid. The deployment state may become set when the fluid hardens. By hardening the fluid, any risks of accidental or natural leakage of fluid may be avoided.

In one form, a reversibly hardenable fluid is introduced. The fluid may be introduced in a liquid form at room temperature and polymerizes (jellifies) into a gel once warmed at body temperature. The fluid might be liquidized again by introducing e.g. cold liquid such as cold saline into the interface. The hardening of the fluid may also arouse as a result of physical means, i.e. light or chemical means, i.e. (catalyzers).

Additionally or alternatively, the at least one actuation element comprises a stent. The stent may be expandable by an inflatable balloon or balloons. In some embodiments three stents may be arranged on a single cylinder balloon or multiple balloons or a shaped balloon.

The stent(s) may be integrated into the outer or inner wall. As previously described, parts of the stent may then serve as the outer or inner wall.

If integrated into the outer wall, parts of the stent(s) serving as an outer wall are more rigid than the rest of the stent(s). The higher rigidity may be achieved through a different material of these parts. Upon activation with e.g. the balloon, the stent(s) will expand in the direction of the less rigid portion and hence inwardly in the direction of the inner wall. Therewith the valve annulus might be adjusted.

Alternatively, the stent(s) is arranged in a space formed between the inner and outer walls. The stent(s) then does not serve as an outer or inner wall itself and therefore, the stent(s) may be constructed with a uniform rigidity all over the stent(s). Because of the higher rigidity of the outer wall, the stent(s) will displace the inner wall upon activation whereas the outer wall basically remains constant.

It is also possible to introduce the stent(s) and/or balloon(s) after the implantation of the tube.

Additionally or alternatively, the at least one actuation element comprises a parallelogram structure, i.e., a "crick".

The crick comprises a basis attached or attachable to or integrated into the outer wall. Two ratchets extend basically perpendicularly to the basis. The ratchets can engage with e.g. two counter ratchets by applying a force. Preferably, the force is applied with an actuator. On top of the ratchets near the inner wall, vis a vis the basis, a further plate is arranged. This further plate is moved inwardly by engaging the ratchets with the counter ratchets.

Alternatively, the further plate is integrally formed with the inner wall. The further plate will then directly displace the valve annulus inwardly upon activation.

Additionally or alternatively the at least one actuation element comprises a pantograph.

The pantograph comprises two side portions and bars which are mechanical linkages connected in a manner based on parallelograms, extending between the side portions. A plate is arranged on top of the bars near the inner wall or integrated into the inner wall. The plate is extending inwardly when at least one side portion is moved towards the other side portion. The parallelograms change their shape during the process but remain parallelograms. Preferably the side portions are moved towards each other. During this moving process, crossing points of the bars basically remain at their positions. The other corners preferably attached to the side portions of the parallelograms move inwardly during the moving process.

Alternatively, the pantograph does not comprise side portions but only mechanical linkage connected bars in a manner based on parallelograms and the plate on top of it. By moving the outer corners of the bars towards each other, the plate is moved inwardly.

The invention further refers to a delivery system, adapted to delivery an annuloplasty device of the invention.

The delivery system preferably comprises a catheter to deliver the annuloplasty device.

BRIEF DESCRIPTION OF THE DRAWINGS

Non-limiting embodiments of the invention are described, by way of example only, with respect to the accompanying drawings, in which.

DETAILED DESCRIPTION OF THE PREFERRED EMBODIMENTS

Figure 1:
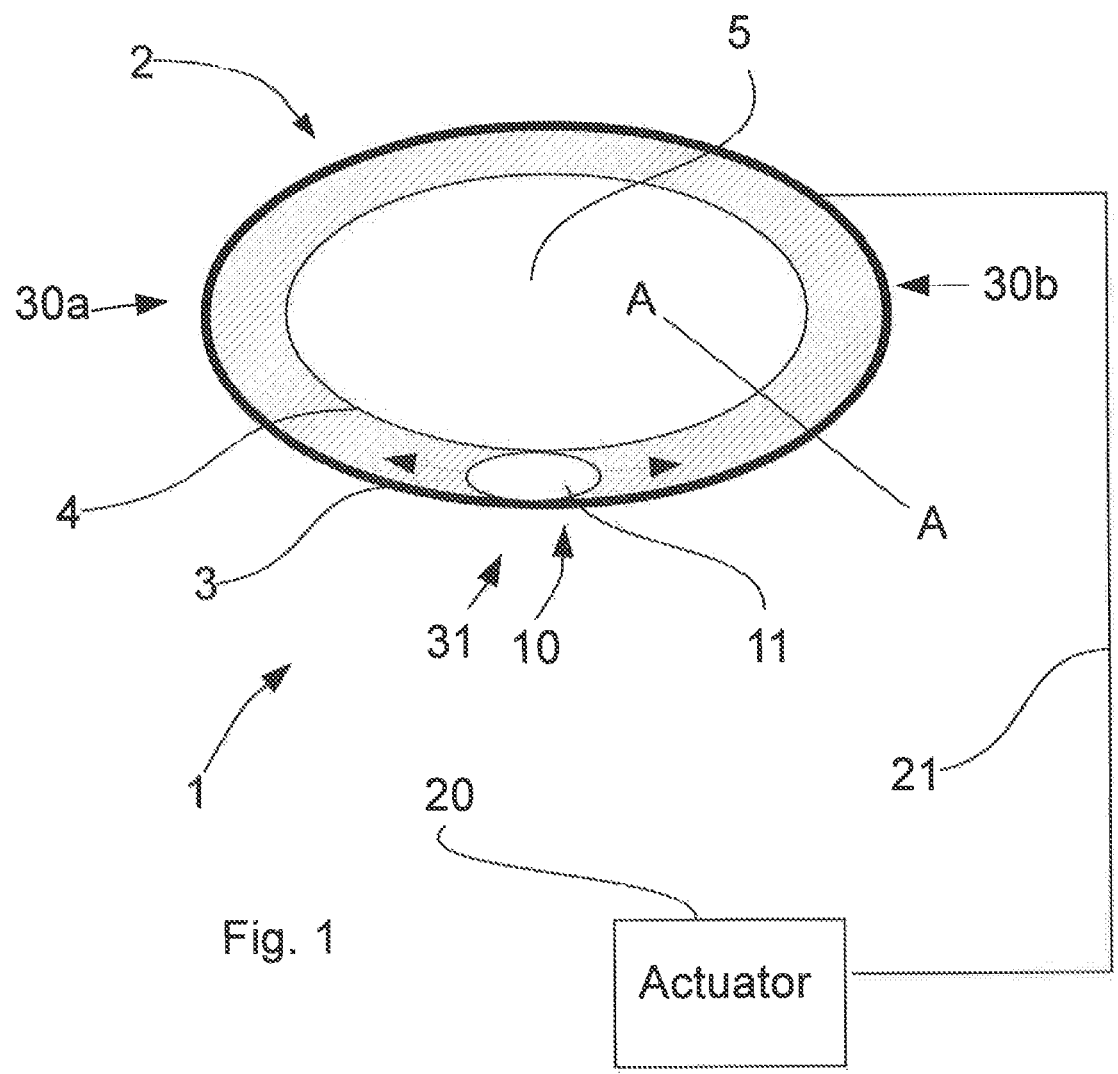
FIG. 1: is a schematic view of an annuloplasty device.

FIG. 1 shows a schematic view of an annuloplasty device 1. The annuloplasty device is arranged as an annular ring with an oval shape which is formed by a tube 2 with a "D" shaped or circular cross section. For a better understanding of the tube 2, the upper half of the tube 2 directed to the viewer is transparent. The tube 2 is made out of Nitinol. An outer wall 3 of the tube 2 is thicker than an inner wall 4 of the tube 2. Through this increased thickness of the outer wall 3 compared to the inner wall 4, the outer wall 3 is more rigid than the inner wall 4.

An actuation element 10 is arranged between the outer wall 3 and the inner wall 4. The actuation element 10 comprises an *inflatable* balloon 11. The balloon 11 is moveable around the circumference of the tube 2 (indicated with arrows). The balloon 11 is expandable with gas. The gas is provided by an actuator 20 over a transmission line 21. When inflated with gas, the balloon 11 expands and displaces the inner wall 4 inwardly towards an inside area 5 of the tube 2. Through the displacement of the inner wall 4, a valve annulus (not shown) to which the device 1 is applied is adjusted. Afterwards, the balloon 11 is deflated and moved to another place, where the balloon 11 may be inflated again. Due to the plastic deformation of the tube, the inwardly displaced wall remains in its expanded position. The inner wall 4 may therewith be displaced at multiple parts. The balloon 11 is inflated at the lateral parts 30a, b and at the posterior part 31 to displace the inner wall 4 and to adjust the valve annulus. The balloon 11 is then removed from the tube 2.

Figure 2:
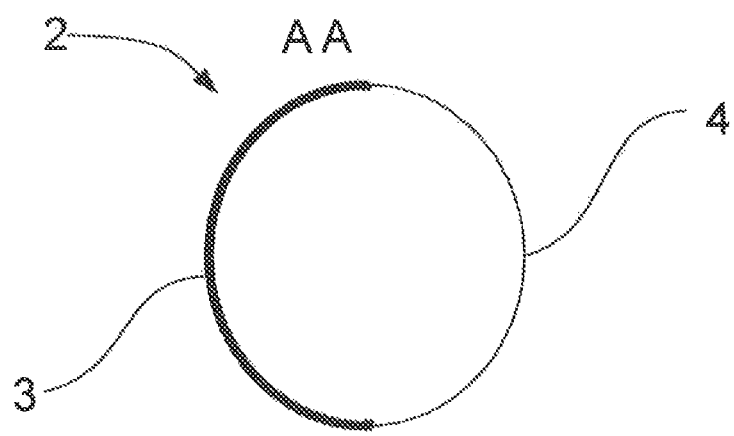
FIG. 2: is a schematic view of a cross section of the annuloplasty device of FIG. 1.

FIG. 2 shows a schematic crosssectional view through the tube 2 in the section AA shown in FIG. 1. The outer wall 3 of the tube 2 is thicker than the inner wall 4 of the tube 2. This provides a difference in rigidity and ensures that only the inner wall 4 is displaced upon activation with the actuation element (see FIG. 1).

Figure 3:
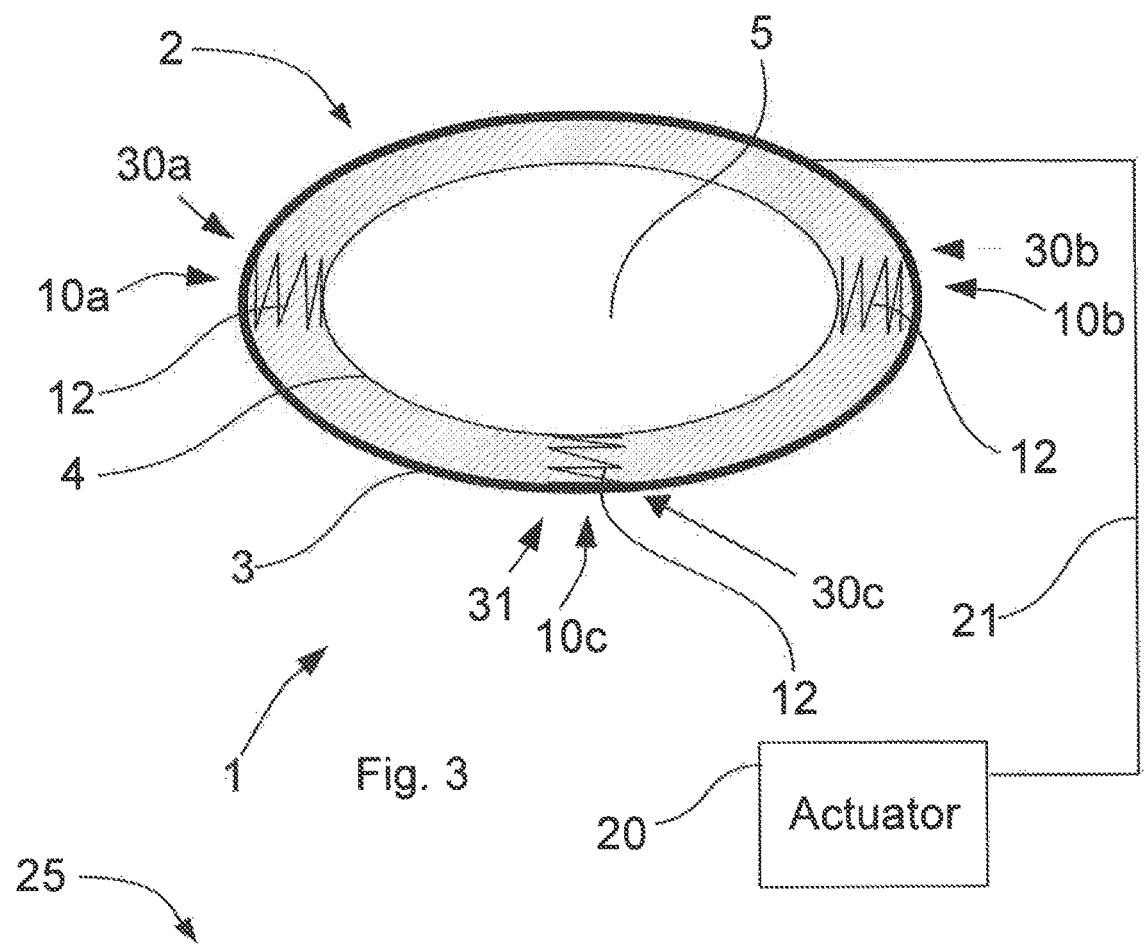
FIG. 3: is a schematic view of an alternative annuloplasty device.

FIG. 3 shows a schematic view of an alternative annuloplasty device 1. Three actuation elements 10a, b, c are arranged in the tube 2 between the inner wall 4 and the outer wall 3. Two actuation elements 10a, b are arranged at lateral portions 30a, b of the tube 2, one actuation element 10c is arranged at a posterior portion 30c of the tube 2. The three actuation elements 10 each comprise a stent 12. The stents 12 have a section integrally formed with the outer wall 3. The stents 12 are expandable with a balloon (not shown). The three stents 12 may be expanded with the same balloon or with a separate balloon each. The balloon is inflated via the actuator 20 and the transmission line 21. The stents 12 expand inwardly because of the part integrally formed with the outer wall 3 is more rigid than the rest of the stent 12. The stents therefore displace the inner wall 4 inwardly and adjust the valve annulus (not shown).

Figure 4:
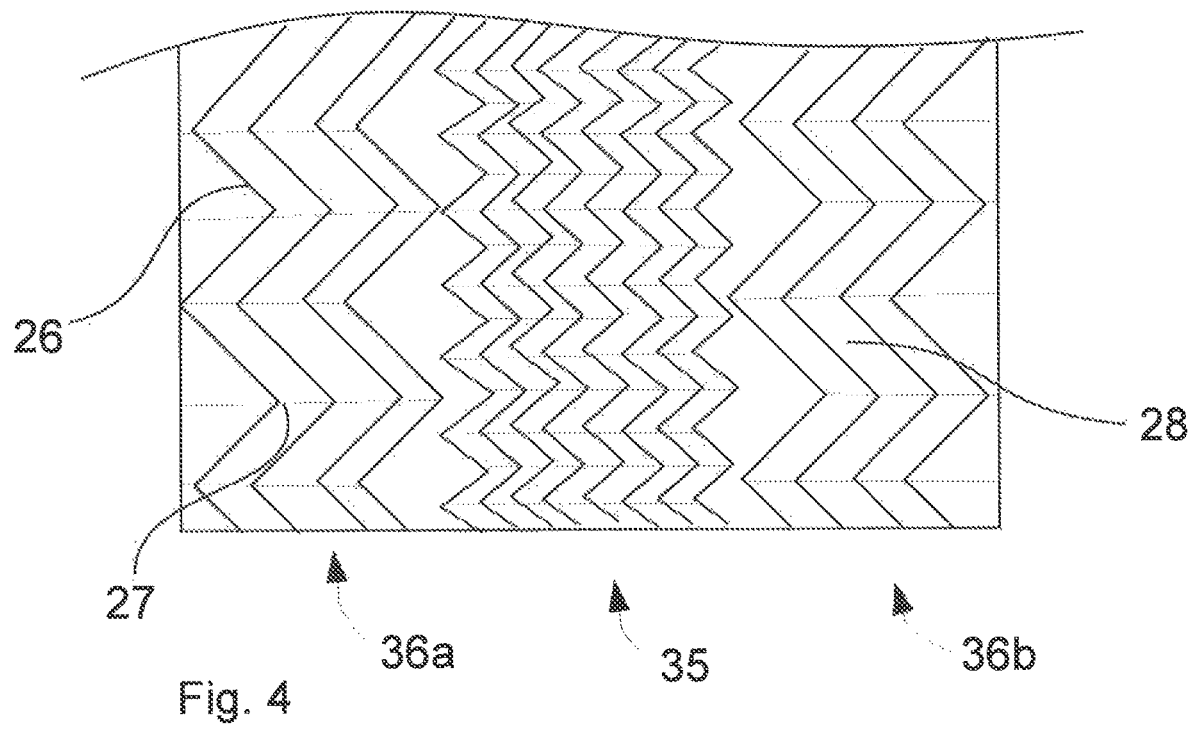
FIG. 4: is a schematic view of a unrolled tube of an annuloplasty device.

FIG. 4 shows a schematic view of an alternative and preferred embodiment of a tube 2 for forming the device 1. The tube 2 is formed as a tube of Nitinol by laser cutting. FIG. 4 shows a developed view of the tube 2. Alternatively the tube 2 might also be rolled out of a basically planar sheet of material. Instead of balloons, mechanical expansion elements are conceivable. The tube 2 comprises multiple horizontal struts 26 and multiple vertical struts 27. The struts 26, 27 are arranged such that the middle section 35 of the plate 25 comprises smaller cells 28 than neighbouring sections 36a, b. The outer sections 36 a, b, will form the inner wall 4 after folding the plate to a tube 2. The middle section 25 will form the outer wall 3. Because of the difference in dimensions of the cells 28 of the sections 35, 36, a difference in rigidity of the outer wall 3 and inner wall 4 will result after folding to a tube 2. The tube 2 thus substantially corresponds to a stent bent into an annular shape and having a more rigid outer wall 3 than an inner wall 4 directed to the centre of the annulus.

Figure 5:
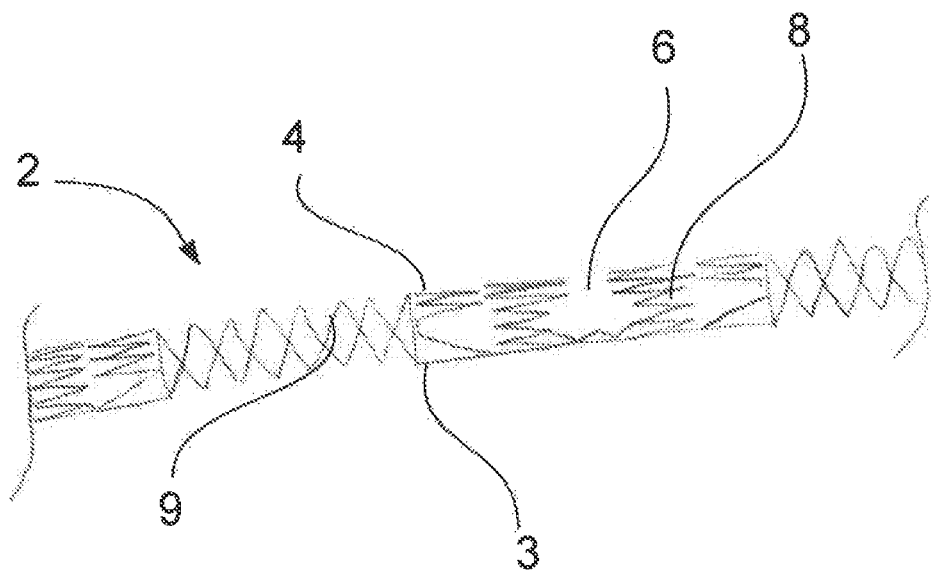
FIG. 5: is a schematic view of a part of an alternative tube in a linear shape.

FIG. 5 shows a part of an alternative tube 2 according to the invention in a linear shape. The tube 2 is made of a superplastic titanium alloy and comprises the inner wall 4 and the outer wall 3. The inner wall 4 is interrupted in three portions 6 (only one is shown in FIG. 5), whereas the outer wall 3 is continuous opposite said interruptions. The tube 2 is formed with bigger cells 8 neighbouring the interruptions 6. The bigger cells 8 form 4 zig-zag structures, two on each side of the interruption 6. The zig-zags are pointing in the direction of the interruption 6. The rest of the tube 2 which connects the bigger cells is formed with two crossing wires arranged in a tubular manner. The inner wall 4 is displaceable in the region of the interruptions 6 with actuation elements, preferably with inflatable balloons (not shown).

Figure 6:
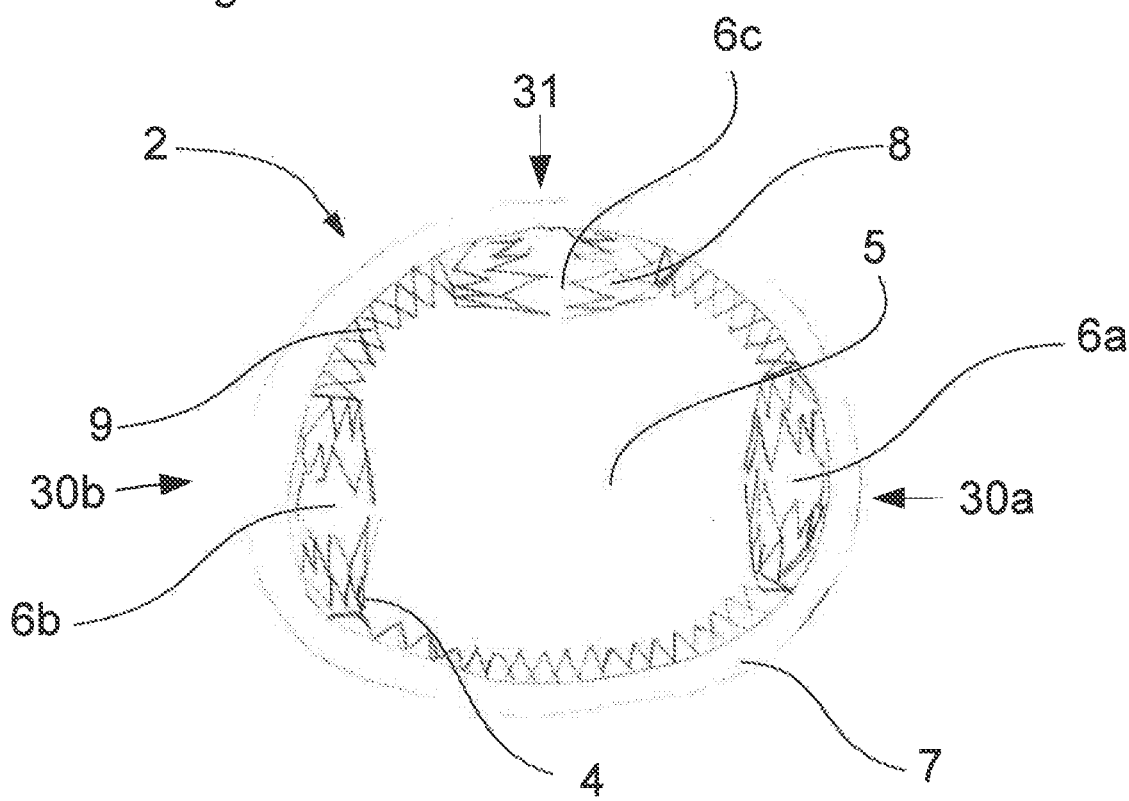
FIG. 6: is a schematic view of the tube of FIG. 5 in an annular shape.

FIG. 6 shows the tube 2 of FIG. 5 brought into an annular shape. The three interruptions 6a, b, c are arranged such that two interruptions 6a, b, are on lateral sides 30a, b, and one interruption 6c is on the posterior side 31. The tube 2 further comprises a fabric tissue 7 serving as an attachment component. The fabric tissue 7 is arranged circumferentially around the tube 2. The fabric tissue can be sutured to the mitral annulus therewith attaching the tube 2 to the annulus. In FIG. 6, the bigger cells 8 next to the interruptions 6 are bent inwardly, i.e. the zig-zag structures are pivoted inwardly around base portions of the zig-zag structures.

The invention claimed is:

1. An adjustable annuloplasty device comprising:
   a tube having an annular shape or adopted to be brought into an annular shape,
   wherein at least one portion of an outer wall or the whole outer wall of the tube is more rigid than at least one opposite portion of an inner wall or the whole inner wall, and
   the inner wall is arranged nearer to an inside area defined by the annular shape than the outer wall, such that the inner wall is adapted to be displaced inwardly at least along the at least one less rigid portion of a circumference upon actuation by at least one actuation element while a perimeter of the outer wall remains constant when the inner wall is displaced inwardly, and
   the inner wall is thinner than the outer wall.

2. The annuloplasty device according to claim 1, wherein the tube has a first shape which is a straight and elongated shape, and the annuloplasty device is adapted to be brought into a second shape which is an annular shape upon release of a delivery system.

3. The annuloplasty device according to claim 1, wherein the inner wall comprises at least one interruption separating the inner wall into at least two portions of the inner wall, at least one outer wall portion opposite the at least one interruption is continuous, and the inner wall is displaceable inwardly next to the at least one interruption upon the activation.

4. The annuloplasty device according to claim 3, wherein the tube comprises larger cells in a region of the interruptions than in the other regions.

5. The annuloplasty device according to claim 1, wherein the tube is formed as a mesh structure with cells, and the inner wall has bigger mesh cells than the outer wall.

6. The annuloplasty device according to claim 1, wherein the outer wall comprises a support ring.

7. The annuloplasty device according to claim 1, wherein the tube comprises a memory shape material.

8. The annuloplasty device according to claim 1, wherein two actuation elements are arranged at opposite lateral portions of the annular tube and one actuation element is arranged at a posterior portion of the annular tube.

9. The annuloplasty device according to claim 1, wherein the actuation element comprises an inflatable balloon, and the device is actuatable with the inflatable balloon.

10. The annuloplasty device according to claim 1, wherein the at least one actuation element comprises a stent.

11. The annuloplasty device according to claim 1, wherein the at least one actuation element is a mechanical actuator element.

* * * * *